United States Patent [19]
Bauer, Jr. et al.

[11] Patent Number: 5,523,480
[45] Date of Patent: Jun. 4, 1996

[54] PROCESS FOR PURIFYING UNSATURATED CARBOXYLIC ACIDS USING DISTILLATION AND MELT CRYSTALLIZATION

[75] Inventors: William Bauer, Jr., Huntingdon Valley; Robert M. Mason, Roslyn; Rita K. Upmacis, North Wales, all of Pa.

[73] Assignee: Rohm and Haas Company, Philadelphia, Pa.

[21] Appl. No.: 219,324

[22] Filed: Mar. 28, 1994

[51] Int. Cl.$^6$ ............................ C07B 35/04; C07C 51/42; C07C 51/00
[52] U.S. Cl. .............................. 562/599; 562/600
[58] Field of Search ...................... 562/599, 600

[56] References Cited

U.S. PATENT DOCUMENTS

| | | | |
|---|---|---|---|
| Re. 32,241 | 9/1986 | Saxer | 62/542 |
| 4,671,857 | 6/1987 | Johnson | 203/51 |
| 4,780,568 | 10/1988 | Pascoe | 562/599 |

FOREIGN PATENT DOCUMENTS

| | | |
|---|---|---|
| 5917 | 1/1977 | Japan . |
| 145044 | 6/1987 | Japan . |
| 639858 | 4/1976 | U.S.S.R. . |

OTHER PUBLICATIONS

N. P. Wynn, Separate Organics by Melt Crystallization, Chem. Eng. Progress, 88(3), 55–57, (1992).
N. P. Wynn, Chem. Eng. Progress, 88(3), 52–60 (1992).
Khim. Prom. (2) 106–109 (1979).
Khim. Prom. (8) 486–488 (1984).

*Primary Examiner*—José G. Dess
*Assistant Examiner*—Rosalynd A. Williams
*Attorney, Agent, or Firm*—Terence P. Strobaugh; Thomas D. Rogerson; Richard A. Haggard

[57] ABSTRACT

A process for the preparation of an α,β-unsaturated $C_3$–$C_6$ carboxylic acid of greater than 98% purity, which combines fractional distillation and melt crystallization procedures.

15 Claims, 3 Drawing Sheets

PROCESS FOR PURIFYING UNSATURATED CARBOXYLIC ACIDS USING DISTILLATION AND MELT CRYSTALLIZATION

BACKGROUND OF THE INVENTION

One process to produce methacrylic acid is the catalytic carbonylation of propylene to give isobutyric acid followed by partial oxidative dehydrogenation to yield methacrylic acid. The crude product from this process is a mixture containing water, isobutyric acid, methacrylic acid, and other components. The water is removed using either azeotropic distillation or solvent extraction followed by distillation to remove the extraction solvent and produce an anhydrous mixture. Methacrylic acid is typically separated from the anhydrous mixture using either distillation or crystallization techniques. In separations involving distillation the physical and chemical property similarities of methacrylic and isobutyric acids typically require a large number of theoretical plates in combination with high reflux ratios to achieve high product purity. Furthermore, use of distillation as a separation technique is complicated by the tendency of methacrylic acid to polymerize while being distilled.

When crystallization techniques are employed in the separation, the combination of low melting point for isobutyric acid and low eutectic temperature for isobutyric/methacrylic acid mixtures require that very low crystallization temperatures be used. Such temperatures made crystallization processes difficult to practice economically.

Japanese Kokai 62-145044A describes a distillation method to obtain purified methacrylic acid through the use of at least four separate distillation towers and an extraction column to remove and purify an extraction solvent and to remove both high and low boiling impurities. Japanese Kokai 52-007917A describes a procedure for separating methacrylic acid from the crude aqueous product of the gas phase dehydrogenation of isobutyric acid in which the crude product is first distilled to remove materials with boiling points less than water and then extracted with a hydrocarbon solvent to remove methacrylic acid and related materials. The solution of hydrocarbon solvent, methacrylic acid, and related materials is distilled stepwise, first to remove residual water and then to remove the hydrocarbon solvent. This process results in a methacrylic acid product composition which is about 97% by weight methacrylic acid.

U.S. Pat. No. 4,780,568 describes purification of an anhydrous mixture of methacrylic acid, isobutyric acid, and other impurities using a staged crystallization separation unit with 3–6 equivalent stages and a secondary recovery section with one or more stages to give high purity methacrylic acid. This process requires very low crystallization temperatures. Russian Patent no. 639,858 describes purification of acrylic and methacrylic acids using a countercurrent flow crystallization process involving low temperatures. N. Wynn in *Chemical Engineering Progress*, 88(3), 52–60 (1992) describes the use of distillation and crystallization together in order to improve product purity. Distillation is used to remove the bulk of the impurities followed by melt crystallization to obtain the final high purity product.

Because these known processes are often costly; difficult to control, and/or provide a less pure product than often desired, there continues to be a need for improved methods to efficiently and cost effectively separate methacrylic acid from mixtures containing isobutyric acid.

SUMMARY OF THE INVENTION

The present invention is a process for the separation of an $\alpha,\beta$-unsaturated $C_3$–$C_6$ carboxylic acid from mixtures of the $\alpha,\beta$-unsaturated $C_3$–$C_6$ carboxylic acid and its saturated homologs which comprises combining fractional distillation and melt crystallization processes in which a high proportion of material is recycled. By "high proportion" is meant that the amount of material recycled exceeds that removed from the process as product by a factor of at least 1.5×. The fractional distillation results in two process streams; an overhead process stream in which the ratio of the unsaturated to saturated carboxylic acid is about 0.1 by weight and a bottoms process stream in which the ratio is about 15. The bottoms stream is fed to a melt crystallizer which results in two additional streams; a product stream of high purity (greater than 98% by weight) $\alpha,\beta$-unsaturated carboxylic acid and a residue stream which is about 80% by weight $\alpha,\beta$-unsaturated carboxylic acid and 20% by weight of saturated carboxylic acid. The overhead stream from the fractional distillation column is recycled back to the reactor and the crystallizer residue stream is recycled back to the fractionation column.

Alternatively, the process steps can be reversed, such that melt crystallization is first employed to isolate pure $\alpha,\beta$-unsaturated carboxylic acid. The melt crystallizer bottoms stream is then fractionationally distilled to provide a saturated carboxylic acid rich stream for recycling to the reactor and a recycle stream rich in $\alpha,\beta$-unsaturated carboxylic acid back to the crystallizer.

DETAILED DESCRIPTION OF THE INVENTION

One embodiment of the present invention is a process for preparing greater than 98% by weight pure $\alpha,\beta$-unsaturated $C_3$–$C_6$ carboxylic acids which comprises a) oxidatively dehydrogenating a $C_3$–$C_6$ saturated carboxylic acid in a reactor to produce a first product stream comprising the $\alpha,\beta$-unsaturated carboxylic acid and the saturated carboxylic acid wherein the weight ratio of $\alpha,\beta$-unsaturated to saturated carboxylic acid is greater than about 0.2;

b) fractionally distilling the first product stream in a distillation unit to produce;

(1) an overhead stream wherein the ratio of $\alpha,\beta$-unsaturated to saturated carboxylic acid is less than that in the first product stream, preferably less than 0.5, most preferably less than 0.1, and   (2) a bottoms stream wherein the weight ratio of $\alpha,\beta$-unsaturated to saturated carboxylic acid is from about 5 to about 200, preferably greater than about 9;

c) feeding the overhead stream into the reactor;

d) melt crystallizing the bottoms stream in a crystallization unit to produce

(1) a second product stream comprising the $\alpha,\beta$-unsaturated carboxylic acid wherein the $\alpha,\beta$-unsaturated carboxylic acid content is greater than about 90%, preferably 98%, by weight of the second product stream and   (2) a mother liquor stream;

e) feeding the mother liquor stream into the distillation unit;

f) melt crystallizing the second product stream in a number of stages sufficient to obtain a final product stream of desired α,β-unsaturated carboxylic acid content, preferably greater than 99.9% by weight; and, g) feeding the final mother liquor from the repeated melt crystallization stages of step f) into the distillation unit.

This process is useful for separating mixtures α,β-unsaturated and saturated carboxylic acids, including but not limited to, methacrylic acid from isobutyric acid, acrylic acid from propionic acid, crotonic acid from butanoic acid, and the like. The process is particularly applicable to separations of methacrylic acid from isobutyric acid and acrylic acid from propionic acid because their similarity in physical/chemical properties such as melting points and boiling points make it difficult to obtain efficient separations using standard distillation and crystallization techniques.

Figure 1:
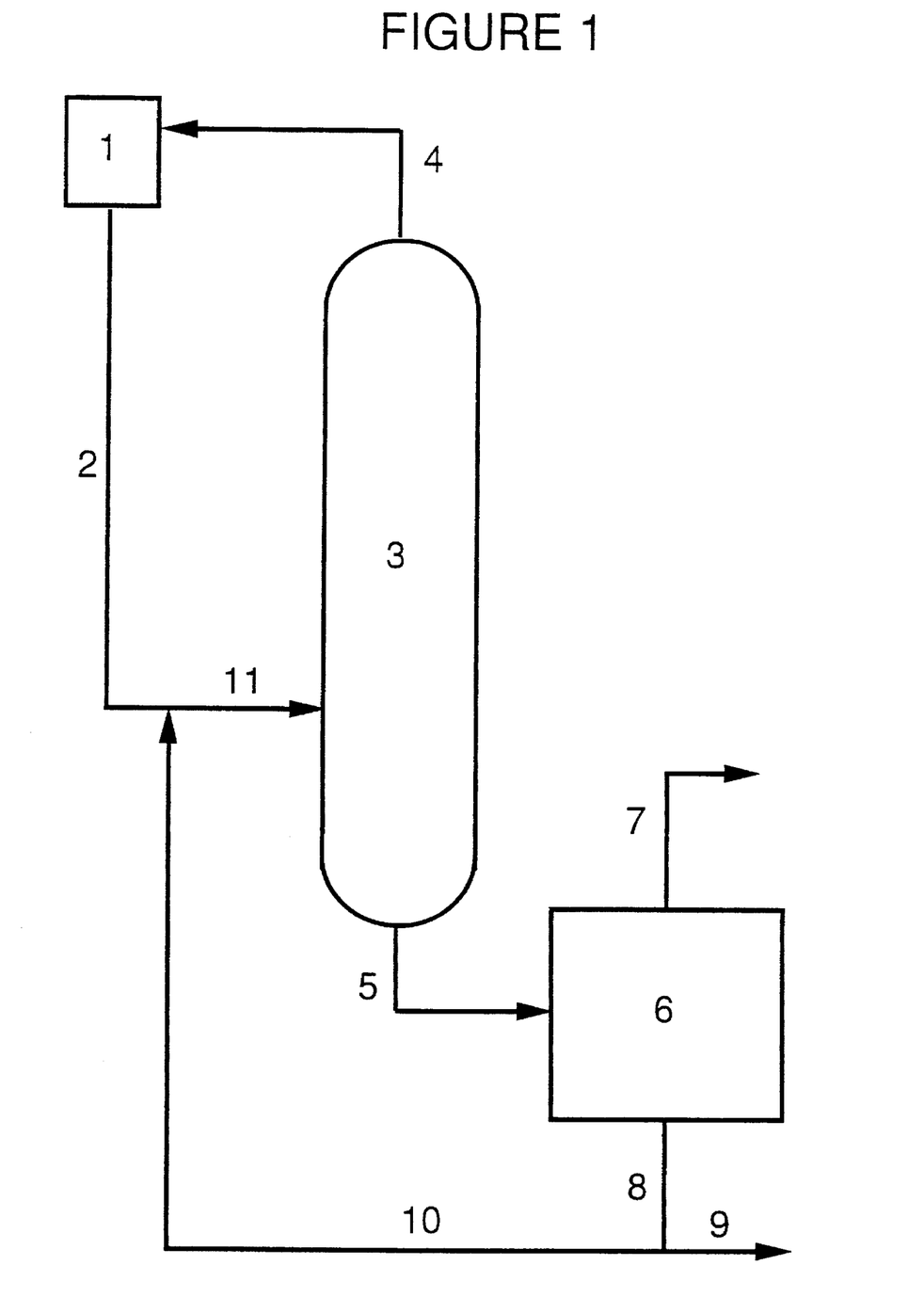
FIG. 1 is a process flow diagram of one embodiment of the invention.

One embodiment of the present invention, exemplified by the separation of methacrylic acid from isobutyric acid, is depicted in FIG. 1. The process of FIG. 1 is preferred when the ratio of α,β-unsaturated to saturated carboxylic acids in the first product stream, from the catalytic dehydrogenation reactor 1, is less than about 15. The first product stream from the catalytic dehydrogenation reactor may contain up to about 40% water. This stream can be fed through line 2 directly into the distillation unit 3 or intermediate steps, such as filtration, extraction, azeotropic distillation, or dehydration, may be accomplished prior to feeding into the unit. The distillation unit 3 configuration is not critical. A high efficiency fractionation column is preferred. Most preferred is a fractionation column which will provide 25–70 theoretical plates at a reflux ratio of 29–355. Operating parameters also are not critical. However, in order to minimize the distillation temperature, low pressures, preferably below 100 mm mercury, are preferred. The stream can be fed into the fractionation column at any convenient point. However, for most efficient operation the composition profile of the column, at steady state, should be determined and the feed should preferably enter at that point where the feed and the steady state column compositions are similar. Distillation results in an overhead stream enriched in isobutyric acid. The balance of the material in the overhead stream is methacrylic acid and low boiling materials which were present in the first product stream. The overhead stream is recycled back into the catalytic dehydrogenation reactor through line 4, recovering what would ordinarily be wasted isobutyric acid resulting in an overall yield increase and lower costs. Another advantage of this process is that neither the catalytic dehydrogenation reaction nor the fractionation need be run under conditions which would result in maximizing the amount of methacrylic acid and minimizing the amount of isobutyric acid produced. The present invention is effective to reduce losses of isobutyric acid in the reactor due to side reactions and losses of methacrylic acid in the fractionation column due to polymerization, again resulting in higher overall yield and lower costs because there is less waste and, therefore, lower operating costs. This is because of the recycling of these materials back to the reactor.

The distillation unit bottoms stream, which contains at least about 90% preferably at least about 95%, by weight methacrylic acid, up to about 10% by weight isobutyric acid, and other minor high boiling impurities, is fed through line 5 into a melt crystallizer 6. Although a batch type crystalizer can be used, a semicontinuous multistage crystallizer such as diagrammed in FIG. 2 whose operation is described below, or similar technology, is preferred. Distillations may also be conducted in a batch manner. However, continuous operation is preferred; continuous operation at steady state is most preferred. In those cases where the distillation unit is operated continuously, a means must be provided to accept the distillation unit bottoms stream when the crystallization unit is operating in a batch or semicontinuous manner. This may be accomplished through the use of a holding tank in line 5, a second crystallization unit, or similar means.

A holding tank or similar means may be incorporated into the mother liquor stream from the crystallization unit feeding the distillation unit through lines 10 or 11 in order to provide a continuous feed to the distillation unit.

In some cases, the vapor pressure of the α,β-unsaturated carboxylic acid may be greater than that of the saturated carboxylic acid. In such cases, the distillate stream from the distillation unit is fed to the crystallization unit while the bottoms stream is recycled back into the catalytic dehydrogenation reactor. The separation of acrylic acid from propionic acid (see Example 10) is such a case.

Figure 2:
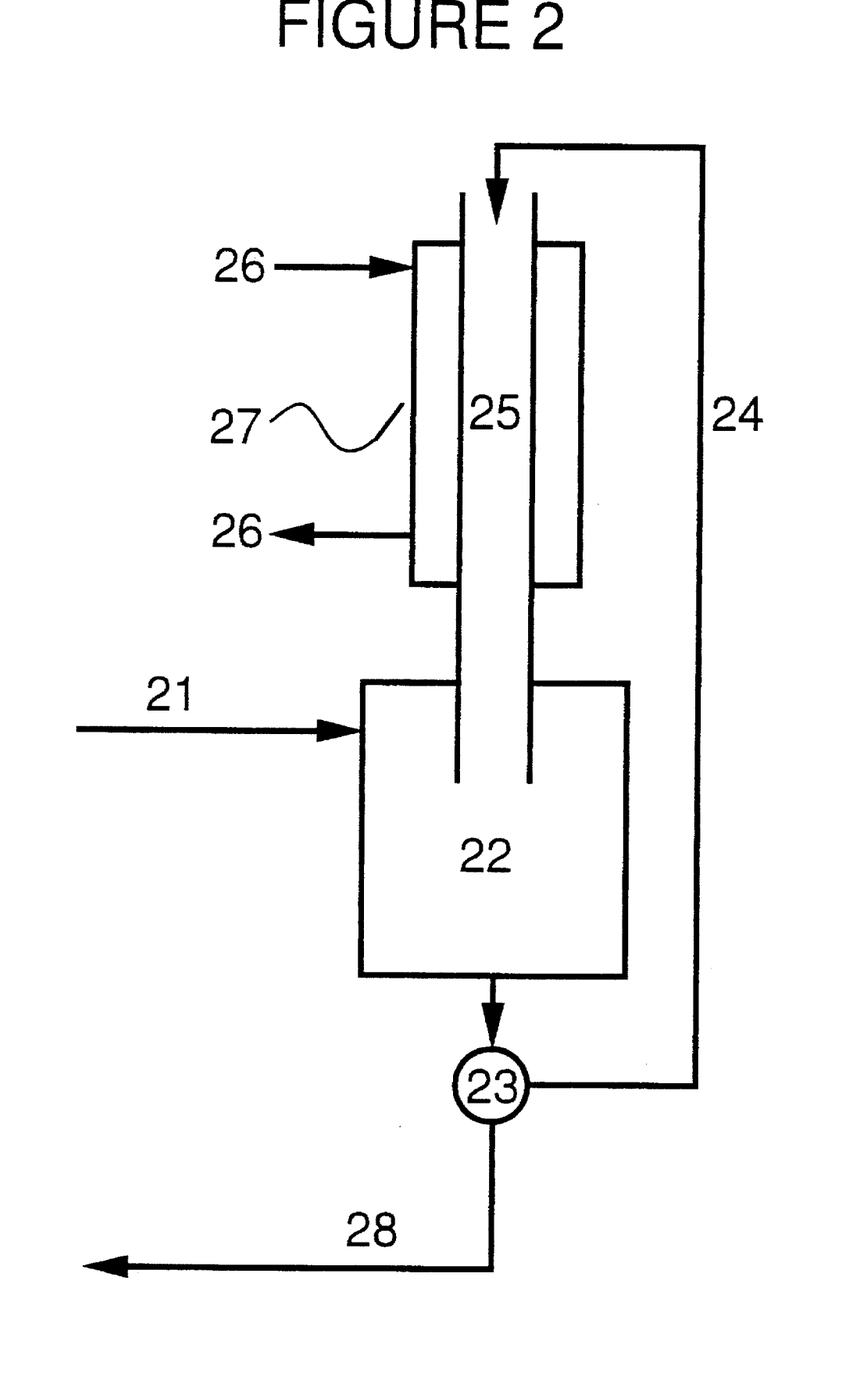
FIG. 2 is a process flow diagram for a laboratory melt crystallizer.
Figure 3:
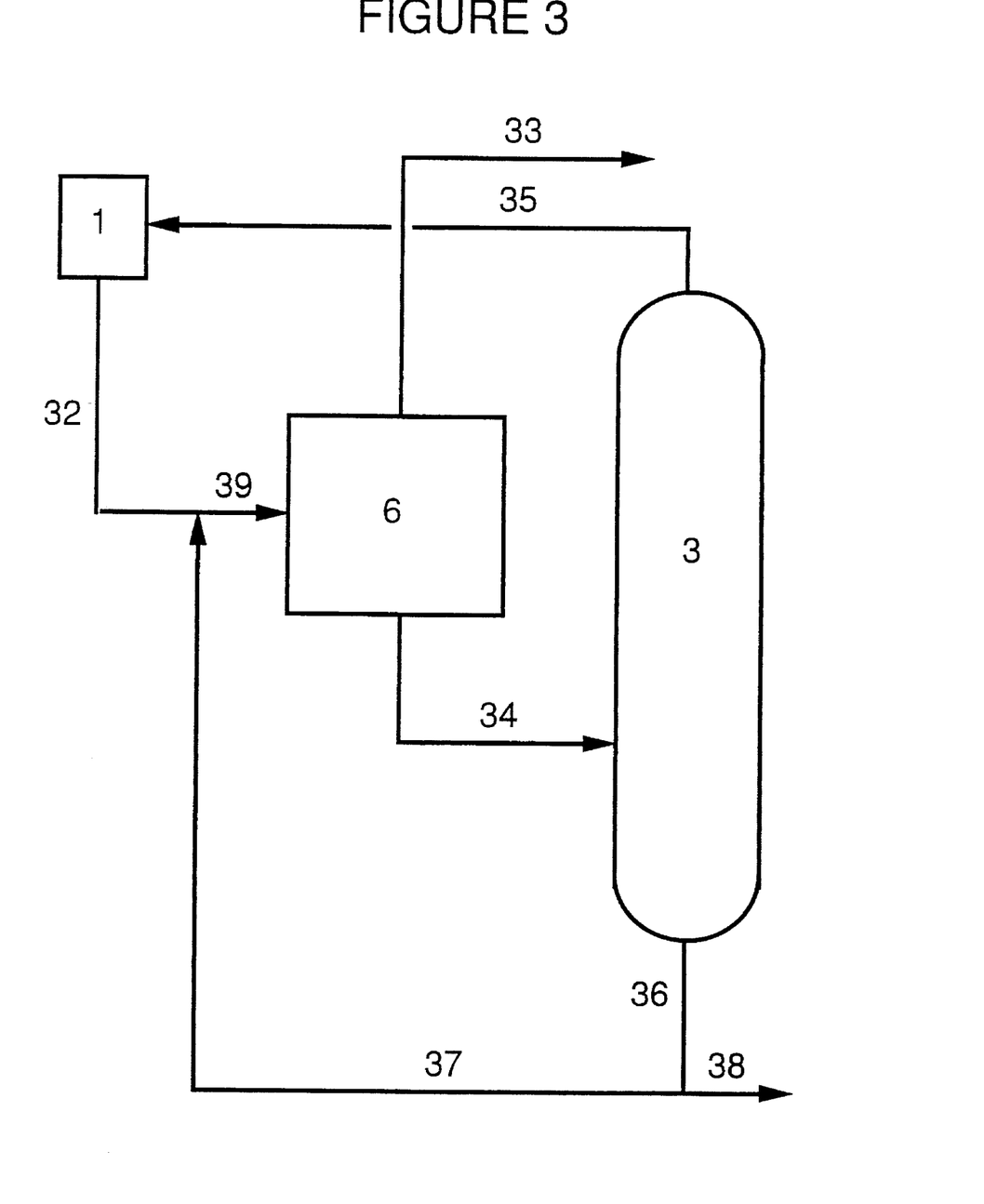
FIG. 3 is a process flow diagram for an alternate embodiment of the invention.

FIG. 2 is a flow diagram of a typical melt crystallizer unit 6, from FIGS. 1 or 3, useable with the present invention. The fractionation column bottoms stream is fed through line 21 (equivalent to line 5 in FIG. 1 and lines 32 or 39 in FIG. 3, described below) into the melt crystallizer collection tank 22 whereupon a circulation pump 23 circulates the stream through line 24 to a crystallization tube 25 back into the collection tank. Under typical crystallization conditions, approximately 50–70% by weight, preferably 60–65% by weight, of the stream is crystallized on the tube walls. The temperature of the tube walls is controlled by circulation of chilled or heated heat transfer fluid 26 through a jacket 27 around the crystallization tube. The desired crystallization temperature will vary with the composition of the stream. For example, a mixture of 0.5% by weight isobutyric acid in methacrylic acid may require a temperature of 14°–15° C. for crystallization whereas a mixture of 6% may require a temperature of 8° C. in order to crystallize 60% by weight of the mixture over a period of 1–1.5 hours. After the feed has crystallized, the mother liquor is removed from the system through line 28 (equivalent to line 10 in FIG. 1 and line 34 in FIG. 3) and is fed to the fractionation column. From about 5% by weight to about 50% by weight, preferably 10–15% by weight, of the crystallized material is then remelted over a period of 1–2 hours by increasing the temperature of the heat transfer fluid. The remelted material (second mother liquor stream) is removed from the system and may also be fed to the fractionation column either separately or combined with the mother liquor. Finally, the crystalline product is recovered, preferably by melting and collecting in the collection tank for a second stage recrystallization or removed from the system as product through line 28 (equivalent to line 7 in FIG. 1 and line 33 in FIG. 3).

Under the conditions described above, the crystallizer 6 produces two streams. The first stream is the final product stream which contains greater than 98% by weight, pure methacrylic acid which is recovered through line 7 (in FIG. 1). By varying the crystallization conditions, for example, the crystallization and remelt temperatures and the feed rate, as well as the number of recrystallization stages, product greater than 99.99% by weight methacrylic acid can be obtained. The second stream is the final mother liquor stream which contains greater than about 80% by weight methacrylic acid and up to about 20% by weight isobutyric acid, as well as other minor, high boiling impurities. The mother liquor stream may be combined with the first product stream through line 10 and fed back into the fractionating column as a combined feed through line 11. Alternately, the mother liquor stream and first product stream may be separately fed to the fractionation column. Occasionally, the mother liquor stream may require purging through line 9 in order to remove heavy impurities. A major advantage in the present process is that the melt crystallizer does not have to be operated under conditions designed to remove the maximum amount of methacrylic acid from the column bottoms stream because since the stream is recycled as the mother liquor stream any methacrylic acid is recovered.

In those cases when the ratio of α,β-unsaturated to saturated carboxylic acids in the first product stream is greater than about 15, the alternative process as diagrammed in FIG. 3 may be used. Again, using methacrylic acid as an example, in this embodiment, the first product stream is fed through line 32 to the melt crystallizer 6 to give a final product stream through line 33 of essentially pure methacrylic acid (greater than about 98% by weight methacrylic acid, preferably greater than about 99.99% by weight methacrylic acid). The mother liquor from the crystallizer, which contains at least about 80% by weight methacrylic acid, is fed through line 34 into the fractionation column 3. The fractionation column provides an overhead stream rich in isobutyric acid which is fed to the reactor 1 through line 35, and a bottoms stream of a mixture of about 95% by weight methacrylic and less than about 5% by weight isobutyric acids which is either combined with the first product stream through lines 36 and 37 and fed back into the melt crystallizer as a combined feed or fed directly into the melt crystallizer. As with the process of FIG. 1, heavy impurities may be removed through lines 36 and 38.

In both variations of the process, neither the fractionation column nor the melt crystallizer are separately operated in a manner which would result in the maximum separation of methacrylic acid from the product stream in each unit. Rather, each is operated in a novel and limited manner such that the combination of fractional distillation and melt crystallization, with two recycle streams in which the bulk of the material is recycled, provides α,β-unsaturated carboxylic acids of high purity (greater than about 99.99% by weight), produces very little waste material, and operates at reasonable temperatures and pressures. This results in an economical, low cost process.

The following examples are provided to illustrate the invention, but do not limit the scope thereof. Unless otherwise specified, all percentages in the examples are expressed as percent by weight.

EXAMPLES

Melt crystallizations are conducted using a laboratory melt crystallizer as described in FIG. 2. Material balances for the fractional distillation step are obtained from computerized steady-state simulations using the FLOWTRAN® program (Monsanto Company) to provide simulations of distillation processes. This program is described in: J. D. Seader, W. D. Seider, and A. C. Pauls, *FLOWTRAN Simulation—An Introduction,* 2nd ed. Cambridge: CACHE, 1977. In the simulation, an ideal solution is assumed for the liquid activity coefficients. The Chao-Seadel correlation is assumed for liquid fugacity and an ideal gas is assumed for the vapor fugacity. In addition, the liquid and vapor fugacities are corrected for organic acid association in the vapor phase by the method described by E. Sebastiani and L. Lacquaniti, *Chem. Eng. Sci.,* 22, 1155 (1967).

Example 1—Melt Crystallization Purification of Methacrylic Acid Containing Approximately 0.5% Isobutyric Acid.

A solution containing 0.49% isobutyric acid ("iBuA") in glacial methacrylic acid is divided into thirds. The first portion is fed to the laboratory melt crystallizer over a period of approximately 1 hour during which time the temperature is decreased from 14.8° C. to 13.8° C. for a first stage crystallization. Approximately 60% of the feed crystallized. The temperature is then increased to a range of from 14° C. to 16° C. over a period of 1.5 hours causing 10% of the crystallized material to remelt. The mother liquor, remelt, and crystallized material are each separately collected and analyzed for iBuA content. The second and third portions are treated in the same manner. Representative results for first stage crystallizations are in Table 1. The methacrylic acid ("MAA") purity and the efficiency of the crystallization are determined by monitoring the iBuA content in the crystallized material.

TABLE 1

| | First Stage Crystallization | | | | | | | |
|---|---|---|---|---|---|---|---|---|
| | Feed | | Mother Liq. | | Remelt | | Crystals | |
| No. | Wt (g)$^a$ | iBuA$^b$ | Wt (g) | iBuA | Wt (g) | iBuA | Wt (g) | iBuA* |
| 1 | 505.8 | 0.49% | 189.0 | 1.094% | 50.1 | 0.314% | 260.3 | 0.0740% |
| 2 | 501.1 | 0.49% | 193.0 | 1.035% | 49.0 | 0.370% | 257.5 | 0.0815% |
| 3 | 504.0 | 0.49% | 192.1 | 1.095% | 62.8 | 0.322% | 249.2 | 0.0720% |
| Total | 1511.0 | 0.49% | 574.1 | 1.075% | 161.9 | 0.334% | 767.0 | 0.0759% |

$^a$Wt (g) = weight in grams
$^b$iBuA = Isobutyric Acid
*Based upon the iBuA content, the crystals are approximately 99.93% pure MAA.

The crystallized portions from the first stage crystallizations are combined and approximately one third fed to the laboratory melt crystallizer and over a period of 50 minutes the temperature is decreased from 17.0° C. to 16.1° C. for a second stage crystallization. Approximately 64% of the feed crystallized. The temperature is then held at 15.7° C. causing 10% of the crystallized material to remelt. Again, the mother liquor, remelt, and crystals are separately collected and analyzed for iBuA content. Representative results for second stage crystallizations are in Table 2.

TABLE 2

| Feed | | Second Stage Crystallization | | | | | |
|---|---|---|---|---|---|---|---|
| | | Mother Liquid | | Remelt | | Crystals | |
| Wt (g)[a] | iBuA[b] | Wt (g) | iBuA | Wt (g) | iBuA | Wt (g) | iBuA* |
| 502.0 | 0.070% | 182.0 | 0.181% | 53.4 | 0.042% | 260.0 | 0.0092% |

[a]Wt (g) = weight in grams
[b]iBuA = Isobutyric Acid
*Based upon the iBuA content, the crystals are at least 99.99% pure MAA.

Example 2—Melt Crystallization Purification of Methacrylic Acid Containing Approximately 5% Isobutyric Acid.

Using the procedure of Example 1, a solution containing approximately 5.8% iBuA in MAA acid is fed into the laboratory melt crystalizer and over a period of approximately 80 minutes the temperature is decreased from 13.5° C. to 8° C. Approximately 62% of the feed crystallized. The temperature is increased to 14.0° C. over approximately 4.7 hours causing 10% of the crystallized material to remelt. The mother liquor, remelt, and crystallized material are each separately collected and analyzed for isobutyric acid content. Representative results of these analyses are in Table 3.

For the following Examples 4–10 and comparison Example 2, distillation column data are simulated with the steady-state process simulator (FLOWTRAN) as described above. Simulator input specifications for each stream are specified in the examples. Melt crystallization (mother liquor, remelt, and crystal amount and purities) data are extrapolated using the results presented in Examples 1–3 above.

TABLE 3

| Feed | | Mother Liquid | | Remelt | | Crystals | |
|---|---|---|---|---|---|---|---|
| Wt (g)[a] | iBuA[b] | Wt (g) | iBuA | Wt (g) | iBuA | Wt (g) | iBuA* |
| 501.1 | 5.675% | 193.0 | 10.30% | 51.7 | 5.44% | 253.6 | 0.950% |

[a]Wt (g) = weight in grams
[b]iBuA = Isobutyric Acid
*Based upon the iBuA content, the crystals are at least 99.05% pure MAA.

Example 3—Melt Crystallization Purification of Acrylic Acid Containing Approximately 0.05% Propionic Acid.

Using the procedure of Example 1, a solution containing approximately 0.05% propionic acid ("PA") in acrylic acid ("AA") is divided into four fractions. Each fraction is fed into the laboratory melt crystallizer over a period of 19–68 minutes at a temperature of about 10° C. Approximately 42% of the feed crystallized. Seven to twenty-seven percent of the crystallized material is remelted over a period of 45–232 minutes. The resulting mother liquor, remelt and crystal fractions are separately combined and analyzed for PA content. Representative results of these crystallizations are in Table 4.

Comparison Example 1—A fresh feed containing 80% MAA and 20% iBuA is fed to a melt crystallizer. The final product specification is set to 0.005% iBuA. To meet this specification, a calculated 4.6 crystallization stages are required. However, the final mother liquor will contain 70.59% MAA which cannot be recycled.

TABLE 4

| Feed | | Mother Liquor | | Remelt | | Crystals | |
|---|---|---|---|---|---|---|---|
| Wt (g)[a] | PA[b] | Wt (g) | PA | Wt (g) | PA | Wt (g) | PA |
| 2600 | 0.047% | 1287 | 0.07% | 168.2 | 0.06% | 1140 | 0.02% |

[a]Wt (g) = weight in grams
[b]PA = Propionic Acid
*Based on the PA content, the crystals are at least 99.98% pure AA.

Example 4—A fresh feed containing 80% (MAA) and 20% iBuA is mixed with the mother liquor stream from the melt crystallizer. The combined stream is fed to the fractionation column. The distillate specification is set at 90% iBuA, the bottoms stream specification is set at 0.5% iBuA, and the final product specification is set at 0.005% iBuA. To meet these specifications, the required number of stages (theoretical plates) in the fractionation column can be 45 (with a reflux ratio of 234) to 55 (with a reflux ratio of 101), assuming an overhead pressure of 30 mm mercury. The required number of crystallization stages is 2.6. Table 5 details the calculated material balance for either of these conditions.

TABLE 5

Example 4 Material Balance

| Component | Fresh Feed | Recycle | Mixed Feed | Distillate | Bottoms | Product |
|---|---|---|---|---|---|---|
| FIG. 1 Ref.* | 2 | 10 | 11 | 4 | 5 | 7 |
| Flow (pph)** | 100.00 | 137.90 | 237.90 | 22.22 | 215.68 | 77.78 |
| MAA % | 80.00 | 99.22 | 91.14 | 10.00 | 99.50 | 99.995 |
| iBuA % | 20.00 | 0.78 | 8.86 | 90.00 | 0.50 | 0.005 |

*Reference to FIG. 1 process flow lines
**pph = pounds per hour

Example 5—The specifications in Example 5 are identical to those in Example 4 except that the specification for iBuA in the bottoms stream is increased to 5.0%. To meet these specifications, the required number of stages in the fractionation column can be 30 (with a reflux ratio of 194) to 40 (with a reflux ratio of 61), assuming an overhead pressure of 30 mm mercury. The required number of crystallization stages is 3.8. Table 6 details the calculated material balance for either of these conditions.

TABLE 6

Example 5 Material Balance

| Component | Fresh Feed | Recycle | Mixed Feed | Distillate | Bottoms | Product |
|---|---|---|---|---|---|---|
| FIG. 1 Ref.* | 2 | 10 | 11 | 4 | 5 | 7 |
| Flow (pph)** | 100.00 | 281.37 | 381.37 | 22.22 | 359.16 | 77.78 |
| MAA % | 80.00 | 93.62 | 90.05 | 10.00 | 95.00 | 99.995 |
| iBuA % | 20.00 | 6.38 | 9.95 | 90.00 | 5.00 | 0.005 |

*Reference to FIG. 1 process flow lines
**pph = pounds per hour

Example 6—The specifications in Example 6 are identical to those in Example 4 except that the specification for iBuA in the bottoms stream is increased to 10.0%. To meet these specifications, the required number of stages in the fractionation column is (with a reflux ratio of 197) to 35 (with a reflux ratio of 42), assuming an overhead pressure of 30 mm mercury and the required number of crystallization stages is 4.2. Table 7 details the calculated material balance for either of these conditions.

TABLE 7

Example 6 Material Balance

| Component | Fresh Feed | Recycle | Mixed Feed | Distillate | Bottoms | Product |
|---|---|---|---|---|---|---|
| FIG. 1 Ref.* | 2 | 10 | 11 | 4 | 5 | 7 |
| Flow (pph)** | 100.00 | 340.96 | 440.96 | 22.22 | 418.75 | 77.78 |
| MAA % | 80.00 | 87.72 | 85.97 | 10.00 | 90.00 | 99.995 |
| iBuA % | 20.00 | 12.28 | 14.03 | 90.00 | 10.00 | 0.005 |

*Reference to FIG. 1 process flow lines
**pph = pounds per hour

Example 7—The specifications in Example 7 are identical to those in Example 5 except that the fresh feed is set at 60% MAA and 40% iBuA. To meet these specifications, the required number of stages in the fractionation column can be 30 (with a reflux ratio of 136) to 40 (with a reflux ratio of 40), assuming an overhead pressure of 30 mm mercury. The required number of crystallization stages is 3.8. Table 8 details the calculated material balance for either of these conditions.

TABLE 8

Example 7 Material Balance

| Component | Fresh Feed | Recycle | Mixed Feed | Distillate | Bottoms | Product |
|---|---|---|---|---|---|---|
| FIG. 1 Ref.* | 2 | 10 | 11 | 4 | 5 | 7 |
| Flow (pph)** | 100.00 | 200.98 | 300.98 | 44.44 | 256.54 | 55.56 |
| MAA % | 60.00 | 93.62 | 82.45 | 10.00 | 95.00 | 99.995 |
| iBuA % | 40.00 | 6.38 | 17.55 | 90.00 | 5.00 | 0.005 |

*Reference to FIG. 1 process flow lines
**pph = pounds per hour

Example 8—The specifications in Example 8 are identical to those in Example 7 except that the specification for iBuA in the fresh feed is decreased to 10.0%. To meet these specifications, the required number of stages in the fractionation column can be (with a relux ratio of 232) to 40 (with a reflux ratio of 79), assuming an overhead pressure of 30 mm mercury. The required number of crystallization stages is 3.8. Table 9 details the calculated material balance for either of these conditions.

TABLE 9

Example 8 Material Balance

| Component | Fresh Feed | Recycle | Mixed Feed | Distillate | Bottoms | Product |
|---|---|---|---|---|---|---|
| FIG. 1 Ref.* | 2 | 10 | 11 | 4 | 5 | 7 |
| Flow (pph)** | 100.00 | 321.57 | 421.57 | 11.11 | 410.46 | 88.89 |
| MAA % | 90.00 | 93.62 | 92.76 | 10.00 | 95.00 | 99.995 |
| iBuA % | 10.00 | 6.38 | 7.24 | 90.00 | 5.00 | 0.005 |

*Reference to FIG. 1 process flow lines
**pph = pounds per hour

Example 9—The specifications in Example 9 are identical to those of Example 7 except that the specification for iBuA in the fresh feed is decreased to 5.0% and the bottoms stream specification for iBuA is decreased to 0.5%. Furthermore, the alternate procedure of FIG. 3 is used. To meet these specifications, the required number of stages in the fractionation column can be 45 (with a reflux ratio of 355) to 55 (with a reflux ratio of 157), assuming an overhead pressure of 30 mm mercury. The required number of crystallization stages is 3.3. Table 10 details the calculated material balance for either of these conditions.

TABLE 10

Example 9 Material Balance

| Component | Fresh Feed | Bottoms | Mixed Feed | Distillate | Mother Liquor | Product |
|---|---|---|---|---|---|---|
| FIG. 3 Ref.* | 32 | 37 | 39 | 35 | 34 | 33 |
| Flow (pph)** | 100.00 | 247.58 | 347.58 | 5.55 | 253.13 | 94.45 |
| MAA % | 95.00 | 99.50 | 98.21 | 10.00 | 97.54 | 99.995 |
| iBuA % | 5.00 | 0.50 | 1.79 | 90.00 | 2.46 | 0.005 |

*Reference to FIG. 3 process flow lines
**pph = pounds per hour

Example 10—A fresh feed containing 80% AA and 20% PA is mixed with the mother liquor stream from the melt crystallizer. The combined stream is fed to the fractionation column. The distillate specification is set at 9% PA, the bottoms stream specification is set at 70% PA and the final product specification is set at 0.005% PA. To meet these specifications the required number of stages in the fractionation column is 70 with a reflux ratio of 29 assuming an overhead pressure of 1 mm mercury. The required number of crystallization stages is 10.8. Table 11 details the calculated material balance. In this case, since the AA is more volatile than PA, the bottoms stream is recycled to the reactor and the distillate is fed to the crystallizer.

TABLE 11

Example 10 Material Balance

| Component | Fresh Feed | Recycle | Mixed Feed | Distillate | Bottoms | Product |
|---|---|---|---|---|---|---|
| FIG. 1 Ref.* | 2 | 10 | 11 | 5 | 4 | 7 |
| Flow (pph) | 100.00 | 977.54 | 1077.54 | 1048.98 | 28.57 | 71.43 |
| AA % | 80.00 | 90.34 | 89.38 | 91.00 | 30.00 | 99.995 |
| PA % | 20.00 | 9.66 | 10.62 | 9.00 | 70.00 | 0.005 |

*Reference to FIG. 1 process flow lines
**pph = pounds per hour

Comparison Example 2—A fresh feed containing 80% MAA and 20% iBuA is fed to a fractionation column. The distillation specification is set to 99% iBuA and the bottoms stream specification is set to 0.005% iBuA. To meet these specifications the calculated number of stages (theoretical plates) in the fractionation column is 150 with a reflux ratio of 50.6, assuming an overhead pressure of 30 mm mercury.

These examples demonstrate that at steady-state, the amount of material which is recycled is high compared to the amount of product produced. However, the product produced is of high purity. Since the recycled material is not lost but, rather, is recovered as either product or material returned to the dehydrogenation reactor, the overall combination process is unexpectedly efficient.

We claim:

1. A process for preparing an $\alpha,\beta$-unsaturated $C_3$–$C_6$ carboxylic acid of greater than about 98% by weight purity:

a. oxidatively dehydrogenating a saturated $C_3$–$C_6$ carboxylic acid in a reactor to produce a first product stream comprising an $\alpha,\beta$-unsaturated $C_3$–$C_6$ carboxylic acid and the saturated carboxylic acid wherein the ratio of $\alpha,\beta$-unsaturated to saturated carboxylic acid is greater than about 15;

b. feeding the first product stream into a crystallization unit;

c. melt crystallizing the first product stream in the crystallization unit one or more times to produce;
        (1) a second product stream comprising greater than about 98% by weight of the $\alpha,\beta$-unsaturated carboxylic acid; and
        (2) one or more mother liquor streams comprising greater than about 80% by weight of the $\alpha,\beta$-unsaturated carboxylic acid;

d. feeding the one or more mother liquor streams into a distillation unit;

e. fractionally distilling the one or more mother liquor streams in the distillation unit to produce;
        (1) an overhead stream and
        (2) a bottoms stream;

f. feeding the overhead stream into the reactor; and g. feeding the bottoms stream into the melt crystallizer.

2. The process of claim 1 wherein the step of melt crystallizing comprises:

i. crystallizing from about 50% by weight to about 70% by weight of the first product stream;

ii. separating the mother liquor stream;

iii. melting from about 5% by weight to about 50% by weight of the crystals to produce a second mother liquor stream;

iv. separating the second mother liquor streams from the remaining crystals;

v. feeding the mother liquor stream and the second mother liquor stream to the fractional distillation column;

vi. optionally melting the remaining crystals and repeating steps i–v, wherein the melted remaining crystals are used in lieu of the first product stream, a number of times sufficient to obtain greater than 98% by weight of the unsaturated carboxylic acid content in the remaining crystals.

3. The process of claim 1 wherein the ratio of the $\alpha,\beta$-unsaturated to the saturated carboxylic acid in the overhead stream is less than about 0.5.

4. The process of claim 3 wherein the ratio of the α,β-unsaturated to the saturated carboxylic acid in the overhead stream is less than about 0.1.

5. The process of claim 1 wherein the saturated carboxylic acid is selected from propionic, butanoic, and isobutyric acids.

6. The process of claim 1 wherein the saturated carboxylic acid is isobutyric acid.

7. The process of claim 2 wherein the mother liquor stream and the second mother liquor stream are combined prior to feeding to the fractional distillation column.

8. The process of claim 1 wherein the first product stream is dehydrated prior to melt crystallization.

9. The process of claim 1 wherein the α,β-unsaturated carboxylic acid content of the second product stream is greater than about 99.9% by weight.

10. The process of claim 1 wherein means for holding material are incorporated in the lines connecting the distillation unit and the crystallization unit.

11. A process for preparing acrylic acid of greater than about 98% by weight purity comprising the steps of:
   a. oxidatively dehydrogenating propionic acid in a reactor to produce a first product stream comprising acrylic acid and propionic acid wherein the ratio of acrylic to propionic acid is greater than about 15;
   b. feeding the first product stream into a crystallization unit;
   c. melt crystallizing the first product stream in the crystallization unit one or more times to produce
      (1) a second product stream comprising greater than about 98% by weight of acrylic acid; and
      (2) one or more mother liquor streams comprising greater than about 80% by weight of the acrylic acid;
   d. feeding the one or more mother liquor streams into a distillation unit;
   e. fractionally distilling the one or more mother liquor streams in the distillation unit under conditions wherein vapor pressure of acrylic acid is greater than the vapor pressure of propionic acid to produce
      (1) an overhead stream and
      (2) a bottoms stream;
   f. feeding the bottoms stream into the reactor; and
   g. feeding the overhead stream into the melt crystallizer.

12. The process of claim 11 wherein the first product stream is dehydrated prior to melt crystallization.

13. The process of claim 11 wherein the acrylic acid content of the second product stream is greater than about 99.9% by weight.

14. The process of claim 11 wherein means for holding material are incorporated in the lines connecting the distillation unit and the crystallization unit.

15. The process of claim 11 wherein means for holding material are incorporated in the lines connecting the distillation unit and the crystallization unit.

* * * * *